(12) United States Patent  (10) Patent No.: US 9,192,492 B2
Seguin et al.  (45) Date of Patent: Nov. 24, 2015

(54) DEVICE ALLOWING THE TREATMENT OF BODILY CONDUITS AT AN AREA OF A BIFURCATION

(75) Inventors: Jacques R. Seguin, Windsor (GB); Gonzague L. Issenmann, Clichy (FR); Jean Claude Laborde, Toulouse (FR)

(73) Assignee: Jacques Seguin, Paris (FR)

( * ) Notice: Subject to any disclaimer, the term of this patent is extended or adjusted under 35 U.S.C. 154(b) by 1120 days.

(21) Appl. No.: 11/884,114

(22) PCT Filed: Feb. 16, 2006

(86) PCT No.: PCT/IB2006/000305
§ 371 (c)(1), (2), (4) Date: Aug. 10, 2007

(87) PCT Pub. No.: WO2006/087621
PCT Pub. Date: Aug. 24, 2006

(65) Prior Publication Data
US 2008/0215135 A1  Sep. 4, 2008

Related U.S. Application Data

(60) Provisional application No. 60/736,844, filed on Nov. 16, 2005.

(30) Foreign Application Priority Data

Feb. 17, 2005 (FR) ...................... 05 01614

(51) Int. Cl.
*A61F 2/954* (2013.01)
*A61F 2/856* (2013.01)
(Continued)

(52) U.S. Cl.
CPC . *A61F 2/856* (2013.01); *A61F 2/90* (2013.01); *A61F 2/91* (2013.01); *A61F 2/915* (2013.01);
(Continued)

(58) Field of Classification Search
None
See application file for complete search history.

(56) References Cited

U.S. PATENT DOCUMENTS 4,665,906 A  5/1987 Jervis
4,795,458 A  1/1989 Regan
(Continued)

FOREIGN PATENT DOCUMENTS

AU  200151922 A1  8/2001
CA  2 281 775 A1  6/2000
(Continued)

OTHER PUBLICATIONS

Furui, Shigeru M.D., et al., "Hepatic Inferior Vena Cava Obstruction: Treatment for Two Types with Gianturco Expandable Metallic Stents", Interventional Radiology, 1990, 176:665-670.
(Continued)

*Primary Examiner* — Yashita Sharma
*Assistant Examiner* — Rebecca Preston
(74) *Attorney, Agent, or Firm* — Oliff PLC (57) ABSTRACT

The device includes a stent and a separating device, the stent having a number of areas of separation and the separating device being able to be introduced through the wall of the stent at an area of separation. According to embodiments of the invention, each area of separation has a number of separable junctions; the activation of the separating device separates at least one of the separable junctions of the area of separation so as to separate the stent into two stent sections at the area of the bifurcation and to allow the stent sections to further expand to respectively conform to a shape of the main conduit and to a shape of the secondary conduit at the area of the bifurcation.

53 Claims, 5 Drawing Sheets

(51) Int. Cl.
*A61F 2/90* (2013.01)
*A61F 2/91* (2013.01)
*A61F 2/82* (2013.01)
*A61F 2/86* (2013.01)
*A61F 2/915* (2013.01)
*A61F 2/95* (2013.01)
*A61F 2/962* (2013.01)
*A61F 2/958* (2013.01)
*A61F 2/06* (2013.01)

(52) U.S. Cl.
CPC .... *A61F 2/82* (2013.01); *A61F 2/86* (2013.01); *A61F 2/95* (2013.01); *A61F 2/954* (2013.01); *A61F 2/958* (2013.01); *A61F 2/962* (2013.01); *A61F 2002/065* (2013.01); *A61F 2002/825* (2013.01); *A61F 2002/826* (2013.01); *A61F 2002/828* (2013.01); *A61F 2002/9155* (2013.01); *A61F 2002/91541* (2013.01); *A61F 2002/91558* (2013.01); *A61F 2002/91575* (2013.01); *A61F 2210/0014* (2013.01); *A61F 2230/0034* (2013.01); *A61F 2250/001* (2013.01); *A61F 2250/0036* (2013.01); *A61F 2250/0039* (2013.01); *A61F 2250/0071* (2013.01); *A61F 2250/0098* (2013.01)

(56) References Cited

U.S. PATENT DOCUMENTS

| | | | |
|---|---|---|---|
| 4,820,298 A | 4/1989 | Leveen et al. | |
| 5,067,957 A | 11/1991 | Jervis | |
| 5,514,154 A | 5/1996 | Lau et al. | |
| 5,540,713 A | 7/1996 | Schnepp-Pesch et al. | |
| 5,545,210 A | 8/1996 | Hess et al. | |
| 5,562,641 A | 10/1996 | Flomenblit et al. | |
| 5,591,223 A | 1/1997 | Lock et al. | |
| 5,591,226 A | 1/1997 | Trerotola et al. | |
| 5,597,378 A | 1/1997 | Jervis | |
| 5,749,825 A * | 5/1998 | Fischell et al. ................ 600/3 |
| 5,766,237 A | 6/1998 | Cragg | |
| 5,827,321 A | 10/1998 | Roubin et al. | |
| 5,876,434 A | 3/1999 | Flomenblit et al. | |
| 5,888,201 A | 3/1999 | Stinson et al. | |
| 5,891,108 A | 4/1999 | Leone et al. | |
| 5,911,754 A | 6/1999 | Kanesaka et al. | |
| 5,928,217 A | 7/1999 | Mikus et al. | |
| 5,938,697 A | 8/1999 | Killion et al. | |
| 5,964,770 A | 10/1999 | Flomenblit et al. | |
| 6,066,167 A | 5/2000 | Lau et al. | |
| 6,068,655 A | 5/2000 | Seguin et al. | |
| 6,077,298 A | 6/2000 | Tu et al. | |
| 6,093,203 A | 7/2000 | Uflacker | |
| 6,129,755 A | 10/2000 | Mathis et al. | |
| 6,139,536 A | 10/2000 | Mikus et al. | |
| 6,187,034 B1 | 2/2001 | Frantzen | |
| 6,258,117 B1 | 7/2001 | Camrud et al. | |
| 6,306,141 B1 | 10/2001 | Jervis | |
| 6,312,455 B2 | 11/2001 | Duerig et al. | |
| 6,342,067 B1 | 1/2002 | Mathis et al. | |
| 6,348,065 B1 | 2/2002 | Brown et al. | |
| 6,350,277 B1 * | 2/2002 | Kocur ........................ 623/1.11 |
| 6,379,369 B1 | 4/2002 | Abrams et al. | |
| 6,409,754 B1 | 6/2002 | Smith et al. | |
| 6,416,544 B2 | 7/2002 | Sugita et al. | |
| 6,464,720 B2 | 10/2002 | Boatman et al. | |
| 6,478,816 B1 | 11/2002 | Kveen et al. | |
| 6,485,510 B1 | 11/2002 | Camrud et al. | |
| 6,485,511 B2 | 11/2002 | Lau et al. | |
| 6,520,988 B1 * | 2/2003 | Colombo et al. ............ 623/1.35 |
| 6,533,807 B2 | 3/2003 | Wolinsky et al. | |
| 6,540,849 B2 | 4/2003 | DiCarlo et al. | |
| 6,562,067 B2 | 5/2003 | Mathis | |
| 6,568,432 B2 | 5/2003 | Matsutani et al. | |
| 6,572,646 B1 | 6/2003 | Boylan et al. | |
| 6,596,022 B2 | 7/2003 | Lau et al. | |
| 6,602,272 B2 | 8/2003 | Boylan et al. | |
| 6,602,281 B1 | 8/2003 | Klein | |
| 6,602,282 B1 | 8/2003 | Yan | |
| 6,626,937 B1 | 9/2003 | Cox | |
| 6,652,579 B1 | 11/2003 | Cox et al. | |
| 6,666,882 B1 | 12/2003 | Bose et al. | |
| 6,666,883 B1 | 12/2003 | Seguin et al. | |
| 6,679,910 B1 | 1/2004 | Granada | |
| 6,699,280 B2 | 3/2004 | Camrud et al. | |
| 6,706,061 B1 | 3/2004 | Fischell et al. | |
| 6,881,223 B2 | 4/2005 | Penn et al. | |
| 6,887,264 B2 | 5/2005 | Penn et al. | |
| 6,908,479 B2 | 6/2005 | Lau et al. | |
| 6,916,336 B2 | 7/2005 | Patel et al. | |
| 6,949,120 B2 | 9/2005 | Kveen et al. | |
| 7,029,492 B1 * | 4/2006 | Mitsudou et al. ............ 623/1.15 |
| 7,097,658 B2 * | 8/2006 | Oktay ........................ 623/1.2 |
| 7,128,758 B2 | 10/2006 | Cox | |
| 2001/0037146 A1 | 11/2001 | Lau et al. | |
| 2001/0037147 A1 | 11/2001 | Lau et al. | |
| 2001/0041930 A1 | 11/2001 | Globerman et al. | |
| 2001/0044648 A1 | 11/2001 | Wolinsky et al. | |
| 2001/0056298 A1 | 12/2001 | Brown et al. | |
| 2002/0107560 A1 * | 8/2002 | Richter ........................ 623/1.11 |
| 2003/0045923 A1 | 3/2003 | Bashiri | |
| 2003/0050688 A1 | 3/2003 | Fischell et al. | |
| 2003/0078649 A1 | 4/2003 | Camrud et al. | |
| 2003/0083731 A1 | 5/2003 | Kramer et al. | |
| 2003/0114912 A1 | 6/2003 | Seguin et al. | |
| 2003/0125791 A1 | 7/2003 | Seguin et al. | |
| 2003/0139796 A1 | 7/2003 | Seguin et al. | |
| 2003/0139803 A1 | 7/2003 | Seguin et al. | |
| 2003/0187497 A1 | 10/2003 | Boylan et al. | |
| 2003/0216804 A1 | 11/2003 | DeBeer et al. | |
| 2004/0002753 A1 | 1/2004 | Burgermeister et al. | |
| 2004/0006381 A1 | 1/2004 | Seguin et al. | |
| 2004/0059410 A1 | 3/2004 | Cox | |
| 2004/0093077 A1 | 5/2004 | White et al. | |
| 2004/0098080 A1 | 5/2004 | Lau et al. | |
| 2004/0098091 A1 | 5/2004 | Erbel et al. | |
| 2004/0167616 A1 | 8/2004 | Camrud et al. | |
| 2004/0176837 A1 | 9/2004 | Atladottir et al. | |
| 2004/0243133 A1 | 12/2004 | Materna | |
| 2004/0243220 A1 * | 12/2004 | Gianotti et al. ............. 623/1.15 |
| 2004/0249446 A1 | 12/2004 | Patel et al. | |
| 2005/0015136 A1 | 1/2005 | Ikeuchi et al. | |
| 2005/0033399 A1 | 2/2005 | Richter | |
| 2005/0038500 A1 | 2/2005 | Boylan et al. | |
| 2005/0075716 A1 | 4/2005 | Yan | |
| 2005/0096726 A1 | 5/2005 | Seguin et al. | |
| 2005/0125051 A1 * | 6/2005 | Eidenschink et al. ....... 623/1.12 |
| 2005/0125052 A1 | 6/2005 | Iwata et al. | |
| 2005/0159808 A1 | 7/2005 | Johnson et al. | |
| 2005/0182479 A1 | 8/2005 | Bonsignore et al. | |
| 2005/0192663 A1 | 9/2005 | Lau et al. | |
| 2005/0209670 A1 * | 9/2005 | George et al. ................ 623/1.11 |
| 2005/0222671 A1 | 10/2005 | Schaeffer et al. | |
| 2006/0004437 A1 | 1/2006 | Jayaraman | |
| 2006/0015171 A1 | 1/2006 | Armstrong | |
| 2006/0015172 A1 | 1/2006 | Boyle et al. | |
| 2006/0015173 A1 | 1/2006 | Clifford et al. | |
| 2006/0030931 A1 | 2/2006 | Shanley | |
| 2006/0036315 A1 | 2/2006 | Yadin et al. | |
| 2006/0060266 A1 | 3/2006 | Bales et al. | |
| 2006/0064154 A1 | 3/2006 | Bales et al. | |
| 2006/0064155 A1 | 3/2006 | Bales et al. | |
| 2006/0069424 A1 * | 3/2006 | Acosta et al. ................ 623/1.12 |
| 2006/0074480 A1 | 4/2006 | Bales et al. | |
| 2006/0085057 A1 | 4/2006 | George et al. | |
| 2006/0095123 A1 | 5/2006 | Flanagan | |
| 2006/0100694 A1 * | 5/2006 | Globerman ................ 623/1.35 |
| 2006/0111771 A1 | 5/2006 | Ton et al. | |
| 2006/0122694 A1 | 6/2006 | Stinson et al. | |
| 2006/0136037 A1 | 6/2006 | DeBeer et al. | |
| 2006/0184231 A1 | 8/2006 | Rucker | |

(56) References Cited

U.S. PATENT DOCUMENTS

| | | |
|---|---|---|
| 2006/0259123 A1 | 11/2006 | Dorn |
| 2008/0306583 A1 | 12/2008 | Bashiri et al. |

FOREIGN PATENT DOCUMENTS

| | | |
|---|---|---|
| EP | 1 034 751 A2 | 9/2000 |
| EP | 1 290 987 | 3/2003 |
| EP | 1 512 381 | 3/2005 |
| EP | 1 523 959 | 4/2005 |
| EP | 1 563 806 | 8/2005 |
| GB | 2 378 137 A | 2/2003 |
| JP | A-8-332231 | 12/1996 |
| JP | A-2000-316983 | 11/2000 |
| JP | A-2002-035136 | 2/2002 |
| JP | A-2002-505149 | 2/2002 |
| JP | A-2002-541909 | 12/2002 |
| JP | A-2003-527214 | 9/2003 |
| WO | WO 01/70294 A2 | 9/2001 |
| WO | WO 0170294 A2 * | 9/2001 |
| WO | WO 01/74273 A1 | 10/2001 |
| WO | WO 01/76508 A2 | 10/2001 |
| WO | WO 03/047651 | 6/2003 |
| WO | WO 2004/017865 | 3/2004 |
| WO | WO 2004/017865 A1 | 3/2004 |
| WO | WO 2004/096092 | 11/2004 |
| WO | WO 2004/110313 A1 | 12/2004 |
| WO | WO 2005/094728 | 10/2005 |
| WO | WO 2006/087621 | 8/2006 |

OTHER PUBLICATIONS

May 30, 2012, Canadian Office Action issued in Canadian Patent Application 2,597,695.

May 10, 2011 Japanese Office Action issued in Japanese Patent Application 2007-555721 (with English Translation).

* cited by examiner

DEVICE ALLOWING THE TREATMENT OF BODILY CONDUITS AT AN AREA OF A BIFURCATION

FIELD OF THE INVENTION

The present invention relates to a device allowing the treatment of bodily conduits at an area of a bifurcation; that is, at an area of the separation of a main conduit into two secondary conduits. It also relates to a method for treating the bodily conduits at an area of a bifurcation, utilizing this device.

The device according to the invention may also be utilized for treating all kinds of bifurcations, particularly vascular bifurcations.

BACKGROUND OF THE INVENTION

Treating stenosis of a bodily conduit by means of a radially expandable tubular implant with a cutout or meshed structure, currently called a "stent", is well known. This device is introduced in the unexpanded state into the conduit to be treated up to the area of the stenosis, and is then expanded, particularly by means of an inflatable balloon, or, when it has an self-expandable structure, is released by a sheath that contains it in its contracted state.

In particular, the use of one or two stents to treat a bifurcation is known. In the simplest case, a single stent is implanted through the bifurcation (method called "provisional stenting"). In more complex cases, two tubular, stents are positioned according to various methods (called "T-stenting, "culotte," "crush," etc.). These methods, that aim to hold two tubes in the bifurcation, have the disadvantages of involving either a very significant metallic bulk, or a partial and incomplete support of the arterial wall in the "carena," that is, the area where the secondary conduits are connected to each other. Consequently, and in all scenarios, simple tubular stents do not provide good clinical results even if they are coated with an active molecule; in fact, stenosis of the conduits of the bifurcation tends to reappear after several months (restenosis), which involves a new intervention.

It is to be noted that in order to improve blood flow in the secondary duct that is partially obstructed by the stent, the practitioner may introduce a balloon through a mesh of the stent in order to enlarge this mesh. This enlargement is limited by the perimeter of the mesh, which has a smaller diameter than the arterial section in the bifurcation, and therefore does not allow a sufficient opening to be offered.

EP 1,034,751 A2 discloses a balloon expandable stent capable of reducing the degree of inhibition of a blood stream to a branched blood vessel. In the stent, connection portions between adjacent wavy annular members are weaker than other parts and can be broken. In use, the stent may be placed in a blood vessel passing a side branch, and dilated. A balloon may then be inserted through the side wall of the already-dilated stent at the opening to the side branch and inflated, as shown in FIG. 18. As a result, while the stent dilation does not change, connection portions adjacent the balloon are broken to form a hole in the stent side wall almost equal to the inflated diameter of the balloon. Because of the plastic nature of the stent material, the hole remains open, facilitating flow through the side branch. This stent is intended to be used in T-bifurcations, i.e. where the main conduit is straight and the side branch has a much smaller diameter than the main the conduit.

Stents called "dedicated" stents for treating a bifurcation are known from, for example, documents WO 2005/094728, WO 01/074273 or U.S. Pat. No. 6,210,429. In general they have a special feature of having an opening in a portion of the stent in order to allow communication with the secondary conduit without disturbing the blood flow. However, this previously made, single opening necessitates that the stent be placed very precisely longitudinally and angularly in the bifurcation. Different means are provided to facilitate this placement, such as a second guide or a second balloon, but their utilization makes the implantation procedure complex and long, and the placement remains especially uncertain.

Providing a stent in at least two partially separated parts, wherein one, in a truncated form, is designed to be placed in the main conduit, and wherein at least one other, in a cylindrical form, is designed to be placed in a secondary conduit, is known from documents EP 0,909,147 or WO 2004/017865.

However, treatment of a bifurcation with such stents remains a relatively long operation that is difficult and delicate to carry out, particularly considering the necessary precise position of the stent in the bifurcation.

Documents U.S. Pat. No. 6,258,117 or EP 1,290,987 describe stents comprising a plurality of connection structures delimiting portions of the stent between them, these connection structures allow different portions of the stent to be separated after implantation. Said stent portions, therefore released from each other after implantation, allow a better adaptation of the stent to the shape of the bodily conduit treated.

These stents are not adapted to the treatment of a bifurcation and do not solve the aforementioned disadvantage connected to such treatment.

OBJECTS OF THE INVENTION

The object of the present invention is to provide a device allowing said disadvantage to be solved, that is, allowing a bifurcation to be treated in a relatively easy, quick and simple-to-achieve manner, by allowing the creation of a support adapted to the shapes of both conduits.

SUMMARY OF THE INVENTION

The device comprises a stent and a separating means, the stent having a number of areas of separation and the separating means being able to be introduced through the wall of the stent at an area of separation and to exert a separating force, wherein:
 the stent is a self-expanding stent having two states of expansion, a first one in which the stent has a first cross-section area and a second one in which the stent has a second cross-section area, larger than said first cross-section area;
 each area of separation have a number of separable junctions, by which the medial portion of the sent is maintained in the first state of expansion when the ends of the stent are maintained in this first state of expansion;
 the separating force provided by the separating means separates at least one of the separable junctions of said area of separation so as to separate the self-expanded stent into two stent sections at the area of the bifurcation and to allow at least one of the stent sections to further self-expand until said second state of expansion, in which said at least one stent section conforms to a shape of the main conduit and/or to a shape of the secondary conduit at the area of bifurcation.

The separable junctions are preferably relatively weak junctions, which are breakable under the separating force of the separating means but which are designed so that they do not separate as a result of normal bodily stresses on the stent.

Said relatively weak portions are preferably provided in a regular annular arrangement around the stent.

A plurality of said areas of separation is preferably provided longitudinally along the stent.

Therefore, with the device according to the invention, the stent is brought to the level of the bifurcation to be treated, is disposed in the bifurcation in such a manner as to be extended both in the principal duct and in one of the secondary ducts, and is expanded at said first state of expansion; the plurality of areas of separation allows a leeway in the longitudinal positioning of the stent in the bifurcation and in choosing the area of separation to be separated; said separating means is then engaged through the wall of the stent, at the level of the area of separation that appears to be the most optimal to make an opening in the stent (generally this will be closest to the "carena," that is, the area at the level of which the two secondary ducts are joined near the bifurcation); the separating means is then brought to exert said separating force, in order to separate at least one of the separable junctions of this area of separation, and, doing this, to individualize the two parts of the stent, one extending in the principal duct up to the "carena" and the other extending in the secondary duct; the part extending in the principal duct up to the "carena" then expands in the bifurcation until said second state of expansion. It can expand on its own or possibly, but not necessarily, be further expanded by an expansion means such as a balloon.

Positioning of the stent according to the invention involves fewer operations, or may be done by a technique that is easier to implement than existing techniques. The aforementioned leeway in the longitudinal positioning of the stent in the bifurcation and in the choice concerning the area of separation at the level of which the lateral opening of the stent is made are advantageous.

Said areas of separation may be perpendicular to the longitudinal axis of the stent, or may be more or less oblique with relation to the stent. Preferably, said areas of separation are rectilinear, or not rectilinear, for example chevron shaped.

The stent preferably has a structure which has, in said second state of expansion, a cross-sectional area which is at least 125%, for example 200% or more, 300% or more, 400% or more or even 500% or more, more than the cross-sectional area of the stent in said first state of expansion. When the main conduit has a frustoconical shape in the area of the bifurcation, the stent has therefore an unconstrained fully expanded cross-sectional area of at least 125% more than a cross-sectional area of the main conduit at a narrower end of the frustoconical shape.

Preferably, means are provided to ensure the engagement of the separating means through said area of separation. This means may, for example, comprise:
  means for marking each area of separation, particularly in the form of radio-opaque markers; and/or
  a distinctive structure of the portions of the stent situated on each side of said area of separation defining open cells near each area of separation.

Such means may help ensure that the separating means is engaged at the level of an area of separation and not through possible meshes or closed cells that may comprise inseparable portions of the stent; for example a more open mesh structure of the stent portions at an area of separation avoid the risk of inserting the separating means outside of an area of separation.

Each separable junction may, for example, be in the form of a bridge connected to adjacent stent portions. At least one bridge may also comprise one or more weak portions designed to be broken, for example in the form of one or more thinnings of the bridge section, in the form of cuts or perforations, particularly circular, provided in this bridge, in the form of one or more grooved or striated areas, in the form of two parts forming interconnected hooks, specific for being deformed for separating under the action of the separating means, or in the form of a microlever type microelectromechanical system (called "MEMS"), particularly specific for being opened with the help of a cryotherapy balloon cooling these microlevers.

Methods of treating a bifurcation according to the invention comprise the following steps:
  a. inserting a self-expanding stent through a conduit into the area of bifurcation and locating the stent partially in the main conduit and partially in a secondary conduit;
  b. allowing the stent to self-expand; and
  c. at least partially separating the self-expanded stent into two stent sections at the area of bifurcation and allowing the stent sections to further self-expand to respectively conform to a shape of the main conduit and to a shape of the secondary conduit at the area of bifurcation.

Preferably, the step a. comprises bending the stent at least 10 degrees, for example at least 10, 15, 20, 30 or 40 degrees, between the main conduit and the secondary conduit.

Preferably, the area of bifurcation has a Y-shape where the main conduit divides into two said secondary conduits.

Preferably, the area of bifurcation has a T-shape and step a. comprises bending the stent around a juncture between a stem and a cross piece of the T-shape.

Preferably, the step c. comprises allowing the stent section that remains in the main conduit to expand to conform to and support a frustoconical shape of the main conduit at the area of bifurcation.

Preferably, the step c. comprises breaking the stent sections at relatively weak portions of a wall of the stent.

Preferably, said relatively weak portions are provided in a regular annular arrangement around the stent.

Preferably, a plurality of said annular arrangements around the stent are provided longitudinally along the stent.

Preferably, said relatively weak portions of a wall of the stent do not separate as a result of normal bodily stresses on the stent.

Preferably, the step c. comprises completely separating the stent into two detached sections.

Preferably, the step c. comprises only partially separating the stent into two attached sections.

Preferably, said stent is separated around at least 20% of its circumference.

Preferably, the step c. comprises inserting a separating means through a wall of said stent and expanding said separating means to separate said stent into said two sections.

Preferably, the main conduit has an expanding frustoconical shape in the area of bifurcation, and said method further comprises selecting as said stent a stent with an unconstrained fully expanded cross-sectional area of at least at least 125%, for example 200% or more, 300% or more, 400% or more or even 500% or more, more than a cross-sectional area of the main conduit at a narrower end of the frustoconical shape.

Methods of treating a bifurcation according to the invention comprise the following steps:
  a. inserting a stent through said lumen into the area of bifurcation and locating the stent partially in the main conduit and partially in a said secondary conduit with a bend in the stent of at least 10 degrees, for example at least 10, 15, 20, 30 or 40 degrees, between the main conduit and the secondary conduit;
  b. causing the stent to expand; and
  c. at least partially separating the expanded stent into two stent sections at the area of bifurcation and causing the stent sections to further expand to respectively conform to a shape of the main conduit and to a shape of the secondary conduit at the area of bifurcation.

Preferably, said stent is a self-expandable stent, and the stent is caused to expand in step b. by releasing the stent from a constraint against self-expansion.

Preferably, said stent is a self-expandable stent, and the stent is caused to expand in step c. by the act of separating the stent into two sections and thereby releasing newly separated ends of the stent sections to self-expand.

Preferably, the step c. comprises causing the stent section that remains in the main conduit to expand to conform to and support a frustoconical shape of the main conduit at the area of bifurcation.

Preferably, the step c. comprises breaking the stent sections at relatively weak portions of a wall of the stent.

Preferably, said relatively weak portions of a wall of the stent do not separate as a result of normal bodily stresses on the stent.

Preferably, the step c. comprises completely separating the stent into two detached sections.

Preferably, the step c. comprises only partially separating the stent into two attached sections.

Preferably, said stent is separated around at least 20%, for example at least 25% or 30%, of its circumference.

Preferably, the step c. comprises inserting a separating means through a wall of said stent and expanding said separating means to break said stent into said sections.

Preferably, the main conduit has an expanding frustoconical shape in the area of bifurcation, and said method further comprises selecting as said stent a stent with an unconstrained fully expanded cross-sectional area at least 125%, for example 200% or more, 300% or more, 400% or more or even 500% or more, more than a cross-sectional area of the main conduit at a narrower end of the frustoconical shape.

DESCRIPTION OF PREFERRED EMBODIMENTS OF THE INVENTION

Figure 1:
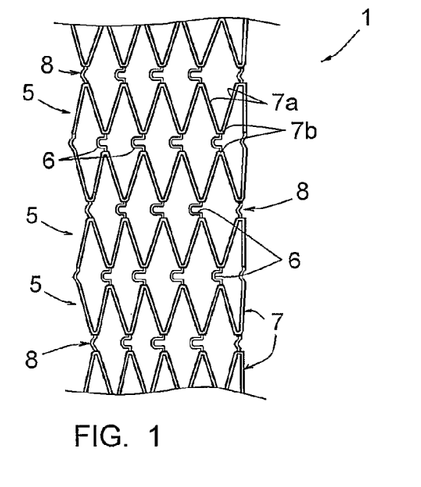
FIG. 1 is a side view of a portion of a stent of the invention; in this view, only the structures situated in the foreground are represented, for clarity of the drawing.
Figure 4:
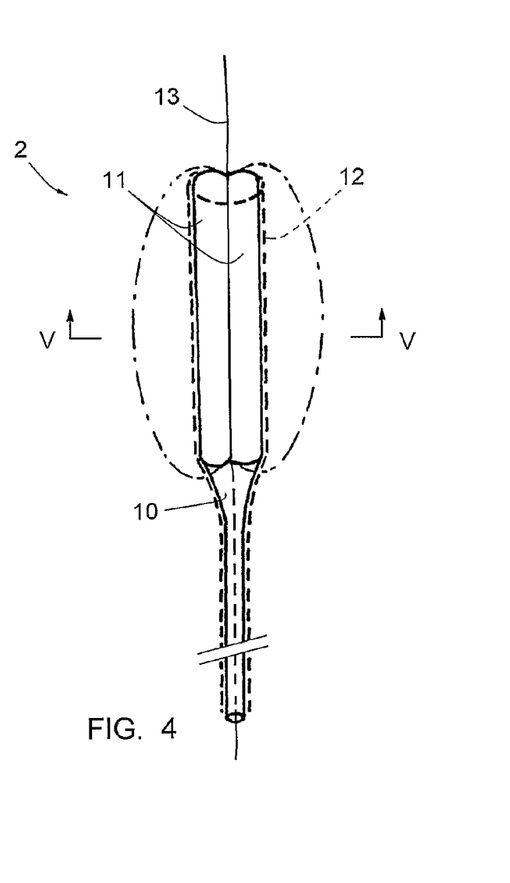
FIG. 4 is a view of a balloon catheter that may be utilized to expand the stent of FIG. 3.

FIG. 1 represents a radially expandable tubular implant 1, currently called a "stent," and FIG. 4 represents a balloon catheter 2 allowing separation of portions of this stent 1 at the area of a bifurcation, that is, at an area of the separation of a principal bodily conduit into two secondary conduits. Stent 1 and catheter 2 form a device allowing treatment of this bifurcation.

Stent 1 in FIG. 1 comprises a plurality of circular (annular) portions 5 in a cutout structure and breakable bridges 6 connecting the circular portions 5 to each other.

Each circular portion 5 is formed by a zigzag portion (e.g., wire) 7 whose extremities are connected to each other. The different segments 7a formed by this wire have substantially identical lengths.

Wire 7 is in a material such that the stent 1 may pass from a radial contraction state to a radial expansion state, by deformation of the bends 7b that define the different segments 7a. The radial contraction state allows engagement of the stent 1 in a sheath used to route this stent to the bifurcation to be treated, and the radial expansion state allows the stent 1 to give the bodily conduit the diameter that the conduit must have. The stent 1 may be self-expandable, that is, it may pass by itself to its radial expansion state when it is released by said routing sheath. The wire 7 may for example be in a shape-memory material such as the nickel-titanium alloy known under the name "nitinol".

Figures 6, 7, 8, 9:
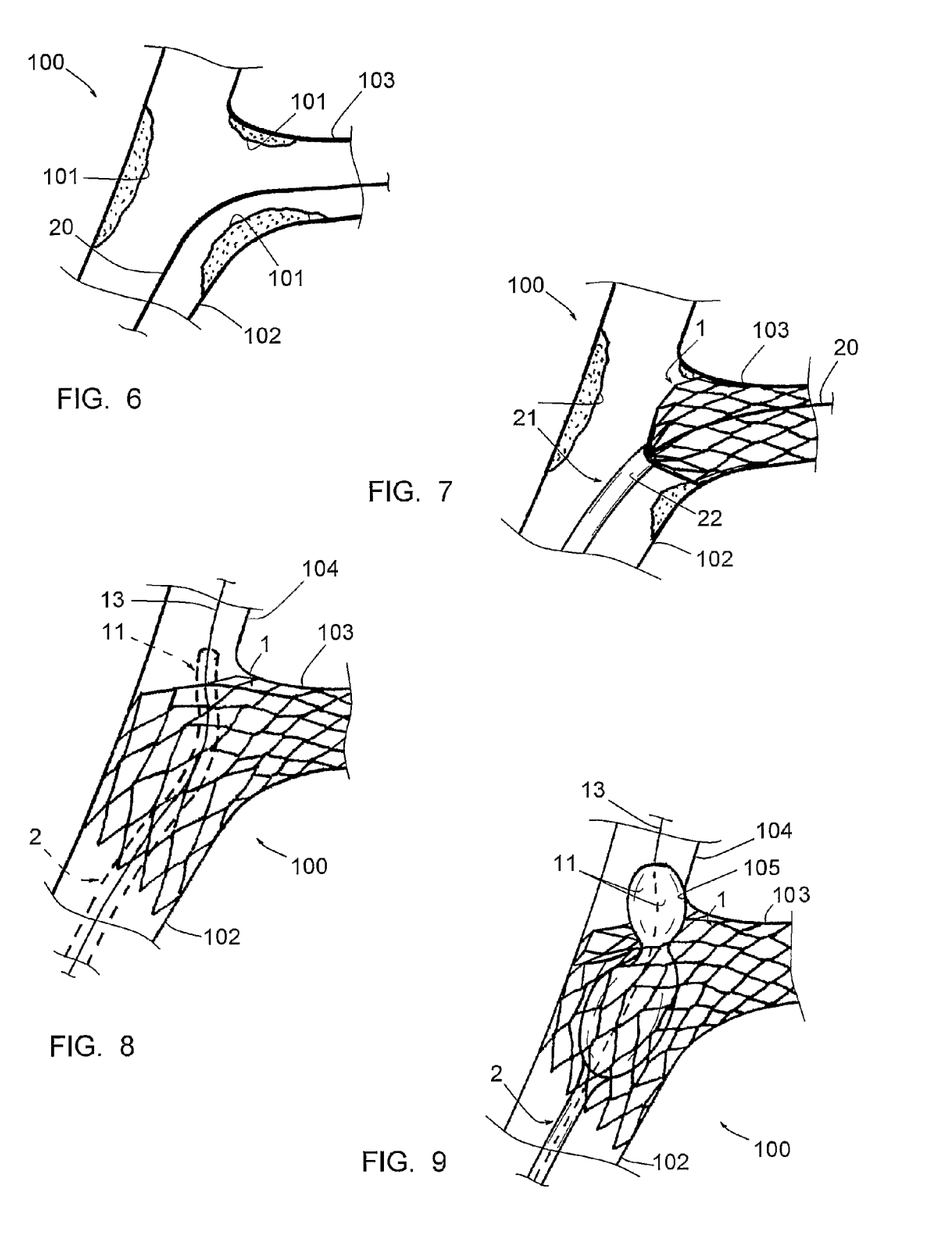
FIGS. 6 to 11 are views of different successive steps of positioning a stent at an area of a bifurcation.

Breakable bridges 6 connect the adjacent bends 7b of two consecutive circular portions 5. In the embodiment shown more particularly in FIG. 2, each of them presents a hat shape, that is, they comprise two lateral branches 6a for connection to the respective bends 7b and a curved central part 6b. Due to this shape, the bridges 6 present a certain flexibility that, in conjunction with the flexibility that the circular portions 5 themselves present, allows the stent 1 to have a certain longitudinal flexibility itself when it is in the radial expansion state, and allows for a bend of at least 10 degrees when placed in the bifurcation. Because of this longitudinal flexibility, as shown in FIG. 8, a part of stent 1 may be engaged in the main conduit of a bifurcation while the other part of this stent is engaged in one of the secondary conduits of this bifurcation even when this main conduit and this secondary conduit form an angle between each other.

Figure 2:
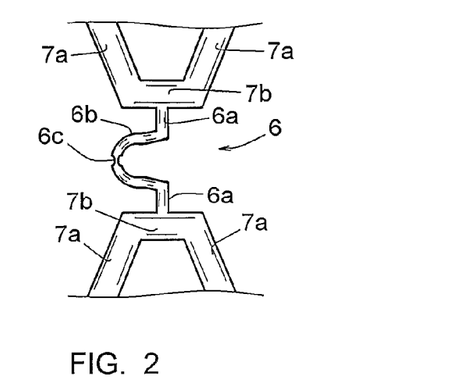
FIG. 2 is a detail view, at a very enlarged scale, of the stent of FIG. 1.

The rounded portion 6b of each bridge 6 of FIG. 2 comprises a reduced median area 6c designed to be broken in order of priority in case of the exercise of a constraint tending to spread the two circular portions 5 apart from each other. The different reduced areas 6c of the bridges 6 situated at the same area in the longitudinal direction of the stent 1 therefore form an area 8 of relative fragility, specific for normally resisting the constraints transmitted by the bodily conduits 102, 103 in which the stent 1 is implanted but not the separation action of the two adjacent portions 5 exerted by the separation means such as a catheter balloon 2 as described below.

Figure 3:
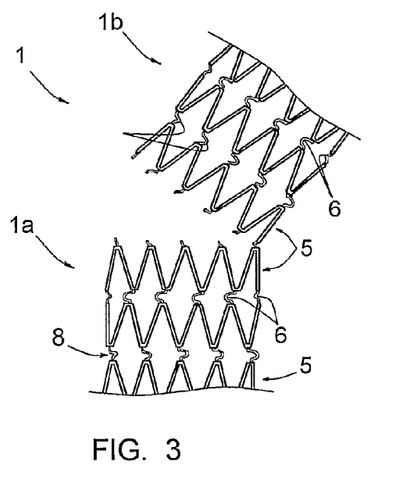
FIG. 3 is a view of a stent that is similar to the stent of FIG. 1, after the lateral opening of the stent by separation of separable bridges that comprise this stent.

As shown in FIG. 3, the breaking of the bridges 6 at an area 8 allows the stent 1 to be largely or completely open according to a significant portion of this area 8 in such a way as to form two independent tubular parts 1a, 1b that are partially separated.

With reference to FIG. 4, the catheter 2 may, for example, comprise an elongated body 10, two side-by-side balloons 11 forming the separation means, and an external sliding sheath 12.

The elongated body 10 presents an axial conduit extending between the balloons 11, that allows the catheter 2 to slide on an axial guiding wire 13.

Figure 5:
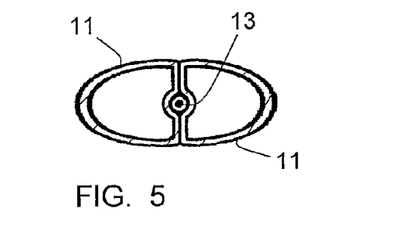
FIG. 5 is a view of the balloons of the balloon catheter of FIG. 4 in transversal section, after inflation.

The two balloons 11 are connected to a source of inflation fluid (not represented). In the deflated state, they are maintained by the sheath 12 in a radial contraction position, represented in solid lines in FIG. 4, and may be inflated until they take the form shown in interrupted lines in FIG. 4 and shown in section in FIG. 5. As shown in this FIG. 5, each balloon 11 presents a section substantially in the shape of a "D" and is bracketed to the other balloon by its plane wall, in such a way that the two balloons 11 conjointly form a balloon having a substantially annular shape in transversal section.

In practice, for the treatment of a bifurcation 100 comprising atheroma plaques 101, a guiding wire 20 is first of all introduced percutaneously through the main conduit 102 and the secondary conduit 103 to be treated (see FIG. 6).

A catheter 21 is then engaged in the main conduit 102 then the secondary conduit 103 by being guided by the wire 20, this catheter 21 comprising the stent 1 maintained in a state of radial contraction such as by an exterior sliding sheath 22; when the distal extremity of the catheter 21 is inside the secondary conduit 103, the sheath 22 may be slid in such a way as to release the stent 1, which is deployed in the secondary conduit 103 then in the main conduit 102, as shown in FIGS. 7 and 8. This deployment allows the atheroma plaques 101 to be compressed and to consequently give the conduits 102 and 103 the adequate diameters.

The guiding wire 13 is then engaged and slides in the main conduit 102 then, through the openings that the wall of stent 1 presents, in the other secondary conduit 104 of the bifurcation 100, as appears in FIG. 8. This guiding wire, named a guidewire, is advantageously passed through an opening located closest to the "carena" 105, that is, the area of bifurcation 100 corresponding to the departure of the two secondary conduits 103, 104, The zigzag wire structure of portions 5 shown in FIG. 8 defines only the open meshes of the side of areas 8, in such a way that the practitioner is ensured of engaging the guidewire 13 between two portions 5 at area 8. The catheter 2 is then engaged on the guidewire 13 up to this portion, and the balloons 11 are engaged through the stent 1, as shown in interrupted lines in this FIG. 8.

Figure 10:
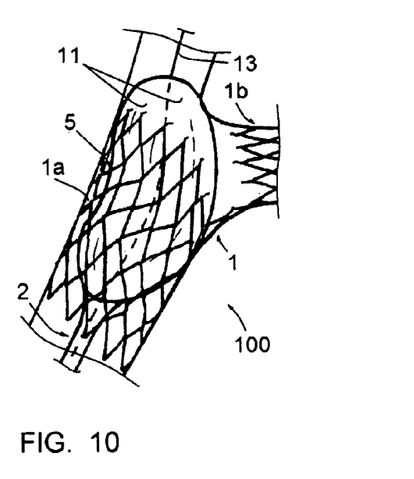

The balloons 11 are then inflated and exert on the two circular portions 5 between which they are engaged a constraint spreading the two portions 5 apart from each other. This inflation causes the rupture of the reduced areas 6c of the bridges 6 situated between these two circular portions 5, with the optional exception of one or more bridges 6 situated diametrically opposed to a bridge at the area of which the balloons 11 crossed stent 1 (see FIGS. 9 and 10), in such a way that the two tubular parts 1a, 1b are thus formed.

Figure 11:
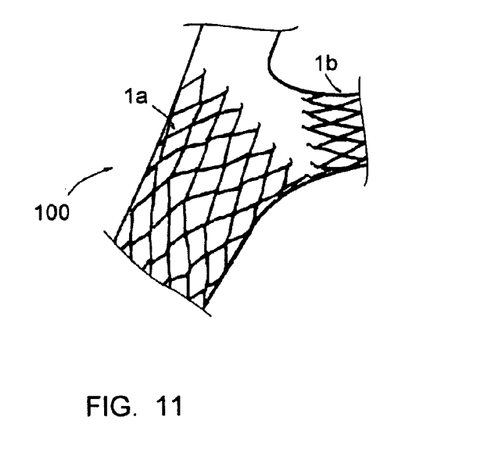

The balloons 11 are then deflated and the catheter 2, and the guiding wire 13, are withdrawn (see FIG. 11).

Figure 12:
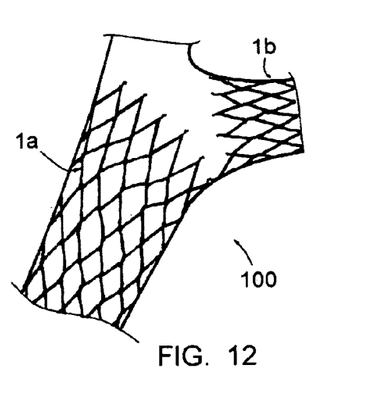
FIGS. 12 and 13 are views of a stent after positioning, according to two other possible positionings of this stent in a bifurcation.
Figure 13:
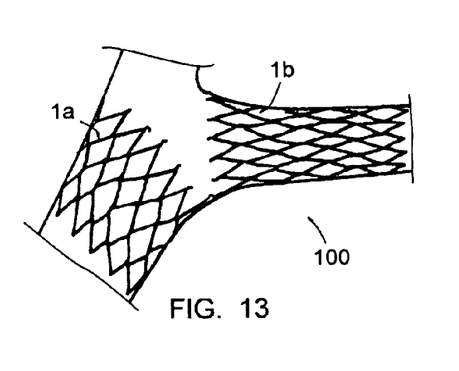

FIGS. 12 and 13 show that a certain leeway in the positioning of the stent 1 in the bifurcation 100 is made possible by the existence of the plurality of areas 8 comprised of the series of bridges 6. It is therefore particularly possible to treat bifurcations 100 having different positionings of atheroma plaques 101.

Figure 14:
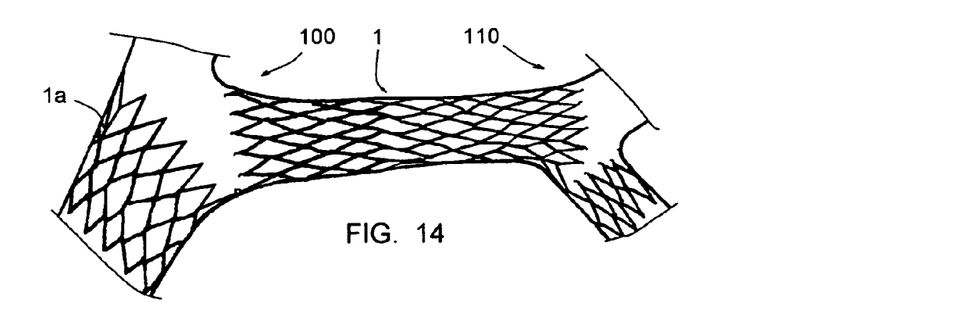
FIG. 14 is a view of a longer stent after positioning in an area of two bifurcations.

FIG. 14 shows that the stent 1 may have a long length and that it may be the subject of two or more lateral openings such as the aforementioned, one at the area of a bifurcation 100 as described above, the other(s) at the area(s) of another bifurcation(s) 110, or that two stents 1 may be positioned successively and opened laterally.

Figure 15:
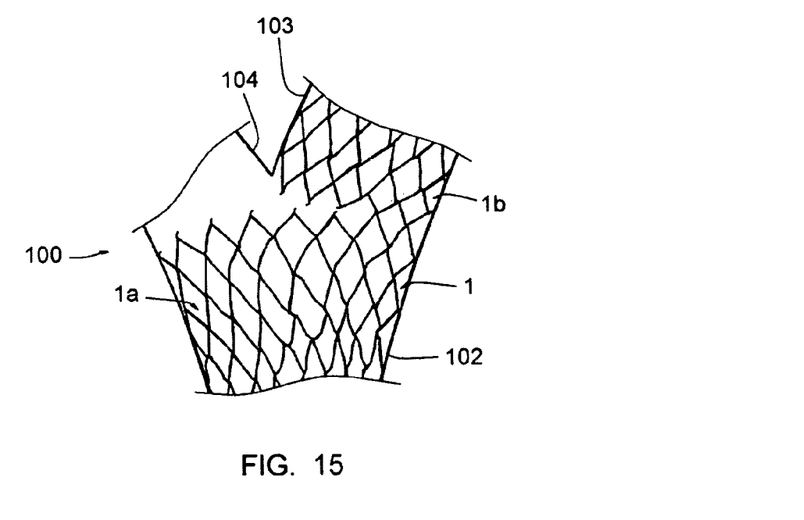
FIG. 15 is a view of a stent in conformance with the invention after positioning in a bifurcation in a transition area between the main conduit and the secondary conduits, the stent portion in the main conduit having a truncated conical form.
Figure 16:
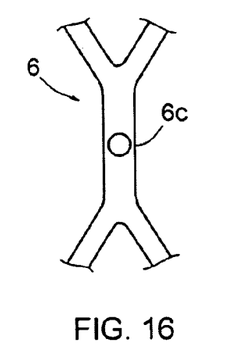
FIGS. 16 to 21 have similar views to FIG. 2 of different variations of embodiment of said separable bridges.
Figure 17:
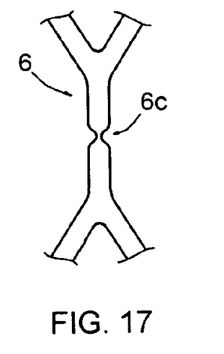
Figure 18:
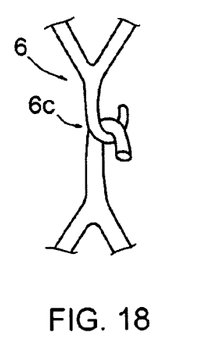

FIG. 15 shows the case of a bifurcation presenting an area of transition that is flared between the main conduit 102 and the secondary conduits 103, 104. Part 1a of the stent 1 may self-expand in such a way as to be adapted to this flared form of this transition area.

Figure 19:
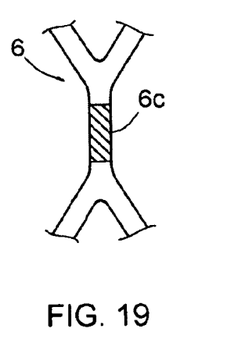
Figure 20:
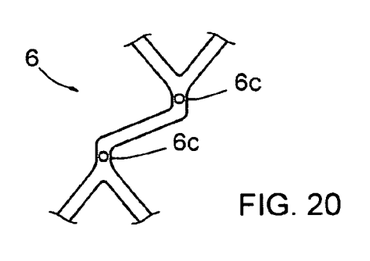
Figure 21:
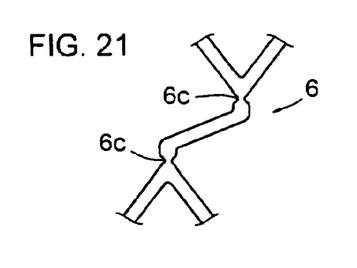

FIGS. 16 to 21 show that each bridge 6 may be parallel to the longitudinal axis of the stent (FIGS. 16 to 19) or oblique with relation to this longitudinal axis (FIGS. 20 and 21).

Each bridge 6 may comprise one or more areas 6c of reduced resistance, for example in the form of one or more thinnings of the section of the bridge or cuts or circular perforations provided in this bridge (FIGS. 16, 17, 20, 21), or of a grooved or striated area.

Each bridge 6 may also or alternatively, for example, comprise one or more areas 6c in a material different from the material constituting the rest of the bridge, suitable for being broken under the separation action exerted by the balloon 11 (FIG. 19). Each bridge 6 may comprise two parts 6b forming interconnected hooks (FIG. 18), specific for being deformed to be separated under the action of separation means, or forming a microlevers-type system (called "MEMS"), specific for being opened with the help of a cryotherapy balloon to cool the microlevers.

As appearing from the aforesaid, the invention provides devices and methods allowing the treatment of bodily conduits at the area of a bifurcation that present the decided advantage of being able to be positioned according to an operation that is shorter and less delicate to carry out than a device according to the prior art.

Figures 22, 23, 24, 25, 26, 27:
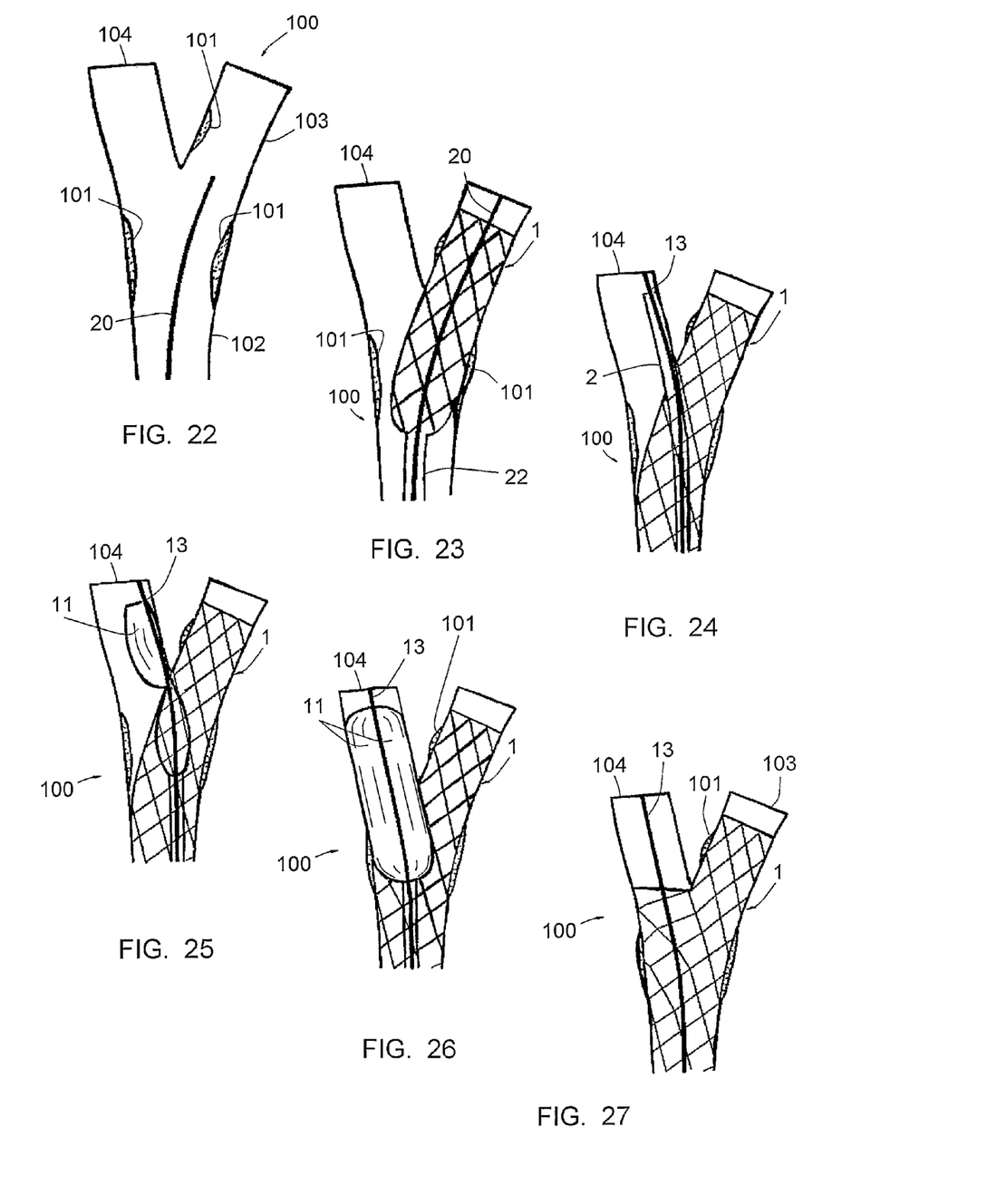
FIGS. 22 to 27 are views of different successive steps of positioning a stent at the area of a Y-shaped bifurcation.

FIGS. 22 to 27 show different successive steps of positioning the stent at the area of a Y-shaped bifurcation. These figures are respectively showing the same steps as the FIGS. 6 to 11. After separation by the balloon on FIG. 26, the stent continues to expand to conform to the shape of the main conduit (FIG. 27). The stent clearly supports the frustoconical shape of the main conduit, which includes part of the side branch ostium.

It goes without saying that the invention is not limited to the embodiment described above by way of example but that it extends to all embodiments of the invention. For example, portions 5 of stent 1 may have a meshed structure; the means provided to ensure the engagement of the balloon through the selected area 8 may comprise marking means for each area 8, for example in the form of radio-opaque markers; the balloon 11 may be formed from two balloons as described previously or from a single balloon; the separation means could be one or more balloons, including cryotherapy balloons, a small expansion tool, like small forceps or pliers, at the distal end of a catheter and actuated from the proximal end with wires extending in the lumen of the said catheter, or other separation means; the stent can be a drug eluted stent.

The invention claimed is:

1. A device allowing treatment of bodily conduits at an area of a bifurcation, the device comprising a stent and a separating means, the stent having a plurality of areas of separation and the separating means being able to be introduced through a wall of the stent at one or more of the plurality of areas of separation and to exert a breaking force;
wherein:
the stent is a self-expanding stent capable of having two states of expansion, a first state in which the stent has a first cross-sectional area and a second state in which the stent has a second cross-sectional area larger than said first cross-sectional area;

each said plurality of areas of separation has a number of bridge structures that form separable junctions, by which a medial portion of the stent is maintained in the first state of expansion when ends of the stent are maintained in this first state of expansion;

the breaking force provided by the separating means is sufficient to break at least one separable junction of said one or more of the plurality of areas of separation so as to break the self-expanded stent into two stent sections at the area of the bifurcation and to allow at least one of the stent sections to further self-expand to said second state of expansion, in which said at least one stent section conforms to a shape of a main conduit and/or to a shape of a secondary conduit at the area of the bifurcation;

the main conduit has an expanding frustoconical shape in the area of the bifurcation; and the second cross-sectional area is at least 125% more than a cross-sectional area of the main conduit at a narrower end of the frustoconical shape.

2. The device according to claim 1, wherein the bridge structures that form separable junctions are relatively weak junctions, which are breakable under the breaking force of the separating means but which do not separate as a result of normal bodily stresses on the stent.

3. The device according to claim 2, wherein said relatively weak junctions are provided in a regular annular arrangement around the stent.

4. The device according to claim 3, wherein said plurality of areas of separation are provided longitudinally along the stent.

5. The device according to claim 1, wherein said plurality of areas of separation are perpendicular to a longitudinal axis of the stent, or are more or less oblique with relation to the stent.

6. The device according to claim 1, wherein said areas of separation are rectilinear.

7. The device according to claim 1, further comprising means to ensure engagement of said separating means through said one or more of the plurality of areas of separation.

8. The device according to claim 7, wherein said means to ensure engagement comprises at least one member selected from the group consisting of:
radio-opaque markers; and
open cells defined on the stent, which are situated on each side of each one of the plurality of areas of separation to ensure an engagement of the separating means through the one or more of the plurality of areas of separation.

9. The device according to claim 1, wherein each bridge structure comprises a bridge connected to adjacent stent portions.

10. The device according to claim 9, wherein at least one said bridge comprises one or more weak portions designed to be broken.

11. The device according to claim 10, wherein said one or more weak portions are in the form of one or more thinnings of the at least one said bridge.

12. The device according to claim 10, wherein said one or more weak portions are in the form of cuts or perforations provided in the at least one said bridge.

13. The device according to claim 10, wherein said one or more weak portions are in the form of one or more grooved or striated areas in the at least one said bridge.

14. A device according to claim 1, further comprising open cells defined on the stent, which are situated on each side of each one of the areas of separation to ensure an engagement of the separating means through said one or more of the plurality of areas of separation.

15. The device according to claim 1, wherein the stent is divided into a proximal region and a distal region at each area of separation such that the proximal and distal regions are only connected by the bridge structures that form the separable junctions at the respective area of separation.

16. A method of treating bodily conduits at an area of a bifurcation, comprising the following steps:
a. inserting a self-expanding stent through a conduit into the area of bifurcation and locating the stent partially in a main conduit and partially in a secondary conduit, the main conduit having an expanding frustoconical shape in the area of bifurcation, and the stent having an unconstrained fully expanded cross-sectional area of at least 125% more than a cross-sectional area of the main conduit at a narrower end of the frustoconical shape;
b. allowing the stent to self-expand after the stent has been inserted at the area of bifurcation;
c. positioning a separating means through a wall of the self-expanded stent at the area of bifurcation and applying a breaking force; and
d. at least partially breaking the self-expanded stent into two stent sections by applying the breaking force at an area of separation of the stent at the area of the bifurcation, the area of separation having a number of bridge structures that form separable junctions that are capable of being broken by the breaking force, and allowing at least one of the stent sections to further self-expand to conform to a shape of the main conduit and/or to a shape of the secondary conduit at the area of bifurcation.

17. A method according to claim 16, wherein step a. comprises bending the stent at least 10 degrees between the main conduit and the secondary conduit.

18. A method according to claim 16, wherein the area of bifurcation has a Y-shape where the main conduit divides into two said secondary conduits.

19. A method according to claim 16, wherein the area of bifurcation has a T-shape and step a. comprises bending the stent around a juncture between a stem and a cross piece of the T-shape.

20. A method according to claim 16, wherein step d. comprises allowing the stent section that remains in the main conduit to expand to conform to and support the frustoconical shape of the main conduit at the area of bifurcation.

21. A method according to claim 16, wherein step d. comprises breaking the stent into the stent sections at relatively weak portions of the bridge structures that form the separable junctions.

22. A method according to claim 21, wherein said relatively weak portions are provided in a regular annular arrangement around the stent.

23. A method according to claim 21, wherein said relatively weak portions do not break as a result of normal bodily stresses on the stent.

24. A method according to claim 16, wherein a plurality of said areas of separation are provided longitudinally along the stent.

25. A method according to claim 16, wherein step d. comprises completely breaking the stent into two detached sections.

26. A method according to claim 16, wherein step d. comprises only partially breaking the stent into two attached sections.

27. A method according to claim 26, wherein said stent is broken around at least 20% of its circumference.

28. A method according to claim 16, wherein step d. comprises expanding the separating means to break said stent into said two stent sections at at least one of the bridge structures.

29. A method according to claim 16, wherein the unconstrained fully expanded cross-sectional area of the stent is at least 300% more than the cross-sectional area of the main conduit at the narrower end of the frustoconical shape.

30. A method according to claim 16, wherein the unconstrained fully expanded cross-sectional area of the stent is at least 500% more than the cross-sectional area of the main conduit at the narrower end of the frustoconical shape.

31. A method for the treatment of a bodily lumen at an area of bifurcation of said lumen where a main conduit of said lumen transitions into at least two secondary conduits, the method comprising the steps:
   a. inserting a stent through said lumen into the area of bifurcation and locating the stent partially in the main conduit and partially in a said secondary conduit with a bend in the stent of at least 10 degrees between a portion of the stent positioned within the main conduit and another portion of the stent positioned within the secondary conduit, the stent being configured with a plurality of bridge structures that form separable junctions, wherein:
      the main conduit has an expanding frustoconical shape in the area of bifurcation, and
      the stent has an unconstrained fully expanded cross-sectional area of at least 125% more than a cross-sectional area of the main conduit at a narrower end of the frustoconical shape;
   b. causing the stent to expand after the stent has been inserted at the area of bifurcation;
   c. positioning a separating means through a wall of the expanded stent at the area of bifurcation and applying a breaking force; and
   d. at least partially breaking the expanded stent into two stent sections by applying the breaking force to the stent at the area of bifurcation, thereby breaking at least one of the plurality of bridge structures and causing the stent sections to further expand to respectively conform to a shape of the main conduit and to a shape of the secondary conduit at the area of bifurcation.

32. A method according to claim 31, wherein said stent is a self-expandable stent, and the stent is caused to expand in step b. by releasing the stent from a constraint against self-expansion.

33. A method according to claim 31, wherein said stent is a self-expandable stent, and the stent is caused to expand in step d. by the act of breaking the stent into the two stent sections and thereby releasing newly separated ends of the stent sections to self-expand.

34. A method according to claim 31, wherein step d. comprises causing a stent section that remains in the main conduit to expand to conform to and support the frustoconical shape of the main conduit at the area of bifurcation.

35. A method according to claim 31, wherein step d. comprises breaking the stent into the stent sections at relatively weak portions of the bridge structures that form the separable junctions.

36. A method according to claim 35, wherein said relatively weak portions of the bridge structures that form the separable junctions do not break as a result of normal bodily stresses on the stent.

37. A method according to claim 31, wherein step d. comprises completely breaking the stent into two detached sections.

38. A method according to claim 31, wherein step d. comprises only partially breaking the stent into two attached sections.

39. A method according to claim 38, wherein said stent is broken around at least 20% of its circumference.

40. A method according to claim 31, wherein step d. comprises expanding said separating means to break said stent into said stent sections at at least one of the bridge structures.

41. A method according to claim 31, wherein the unconstrained fully expanded cross-sectional area of the stent is at least 300% more than the cross-sectional area of the main conduit at the narrower end of the frustoconical shape.

42. A method according to claim 31, wherein the unconstrained fully expanded cross-sectional area of the stent is at least 500% more than the cross-sectional area of the main conduit at the narrower end of the frustoconical shape.

43. A device allowing treatment of bodily conduits at an area of a bifurcation, the device comprising:
   a self-expanding stent capable of having a first state of expansion in which the stent has a first cross-sectional area and a second state of expansion in which the stent has a second cross-sectional area larger than said first cross-sectional area;
   said stent having a plurality of areas of separation, each said plurality of areas of separation comprising a plurality of bridge structures that form separable junctions, by which a medial portion of the stent is maintained in the first state of expansion when longitudinal ends of the stent are maintained in the first state of expansion; and
   a separator configured to apply a breaking force;
   wherein:
      the separator and the stent are configured to permit the separator to be introduced through a wall of the stent at one or more of the plurality of areas of separation when the stent is at least partially self-expanded and to exert the breaking force on the wall of the stent sufficient to break at least one of said bridge structures that form the separable junctions of said one or more of the plurality of areas of separation and break the self-expanded stent into two stent sections at said one or more of the plurality of areas of separation and to allow at least one of said stent sections to further self-expand to said second state of expansion and conform to a shape of a main conduit and/or to a shape of a secondary conduit at the area of the bifurcation,
      the main conduit has an expanding frustoconical shape in the area of bifurcation, and
      the second cross-sectional area is at least 125% more than a cross-sectional area of the main conduit at a narrower end of the frustoconical shape.

44. A device according to claim 43, wherein the bridge structures that form the separable junctions are breakable under the breaking force of the separator, but do not break as a result of normal bodily stresses on the stent.

45. A device according to claim 43, wherein the bridge structures that form the separable junctions are breakable under the breaking force of the separator, but do not break as a result of uniform radial expansion of the stent.

46. A device according to claim 43, wherein the bridge structures that form the separable junctions are breakable under the breaking force of the separator, but do not separate as a result of self-expansion of the stent.

47. A device according to claim 43, wherein the plurality of areas of separation are rectilinear.

48. A device according to claim 43, wherein the plurality of areas of separation are chevron shaped.

49. A device according to claim 43, further comprising radio-opaque markers to ensure an engagement of the separator through said one or more of the plurality of areas of separation.

50. A device according to claim 43, further comprising:
radio-opaque markers; and
open cells defined on the stent, which are situated on each side of each one of the areas of separation;
wherein the radio-opaque markers and open cells ensure an engagement of the separator through said one or more of the plurality of areas of separation.

51. A device according to claim 50, wherein each bridge structure includes at least one weak portion that is configured to be broken under longitudinal strain.

52. The device according to claim 43, wherein the stent is divided into a proximal region and a distal region at each area of separation such that the proximal and distal regions are only connected by the bridge structures that form the separable junctions at the respective area of separation.

53. A method for the treatment of a bodily lumen at an area of bifurcation with a self-expanding stent having a plurality of areas of separation spaced along a longitudinal direction of the stent, each of the areas of separation having a plurality of bridge structures that form separable junctions spaced circumferentially around the respective area of separation, the method comprising the following steps:

a. inserting the self-expanding stent through a conduit into the area of bifurcation and locating the stent partially in a main conduit and partially in a secondary conduit, the main conduit having an expanding frustoconical shape in the area of bifurcation, and the stent having an unconstrained fully expanded cross-sectional area of at least 125% more than a cross-sectional area of the main conduit at a narrower end of the frustoconical shape;
b. allowing the stent to self-expand after the stent has been inserted at the area of bifurcation;
c. positioning a separating means through a wall of the self-expanded stent at one of the plurality of areas of separation located at the area of bifurcation, the separating means configured to apply a breaking force;
d. breaking one or more of the bridge structures that form the separable junctions within the area of separation located at the area of bifurcation by applying the breaking force, the stent being divided into two stent sections extending from the area of bifurcation; and
e. allowing at least one of the two stent sections to further self-expand after one or more of the separable junctions have been broken, wherein the plurality of separable junctions, at areas of separation other than at the area of bifurcation, remain connected.

\* \* \* \* \*